US010881379B2

(12) United States Patent
Villain et al.

(10) Patent No.: US 10,881,379 B2
(45) Date of Patent: Jan. 5, 2021

(54) METHOD OF VISUALIZING A SEQUENCE OF ULTRASOUND IMAGES, COMPUTER PROGRAM PRODUCT AND ULTRASOUND SYSTEM

(71) Applicant: KONINKLIJKE PHILIPS N.V., Eindhoven (NL)

(72) Inventors: Nicolas Francois Villain, Eindhoven (NL); Pascal Allain, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 551 days.

(21) Appl. No.: 15/521,624

(22) PCT Filed: Oct. 21, 2015

(86) PCT No.: PCT/EP2015/074397
§ 371 (c)(1),
(2) Date: Apr. 25, 2017

(87) PCT Pub. No.: WO2016/066497
PCT Pub. Date: May 6, 2016

(65) Prior Publication Data
US 2017/0238905 A1 Aug. 24, 2017

(30) Foreign Application Priority Data

Oct. 27, 2014 (EP) .................... 14306703

(51) Int. Cl.
*A61B 8/00* (2006.01)
*A61B 8/08* (2006.01)
(Continued)

(52) U.S. Cl.
CPC ............ *A61B 8/463* (2013.01); *A61B 8/0883* (2013.01); *A61B 8/14* (2013.01); *A61B 8/466* (2013.01);
(Continued)

(58) Field of Classification Search
CPC ......... A61B 8/14; A61B 8/463; A61B 8/5207; A61B 8/5223; A61B 8/466; A61B 8/0883;
(Continued)

(56) References Cited

U.S. PATENT DOCUMENTS 6,589,176 B2    7/2003  Jago et al.
9,675,320 B2 *  6/2017  Nakata ................. A61B 8/5223
(Continued)

FOREIGN PATENT DOCUMENTS

EP    2397076 A1 * 12/2011 ............... A61B 8/08
JP    2006285064 A    10/2006
(Continued)

OTHER PUBLICATIONS

Buckberg et al "Cardiac Mechanics Revisited" Circulation, Dec. 2008, 118, p. 2571-2587.
(Continued)

*Primary Examiner* — Joel Lamprecht

(57) ABSTRACT

Disclosed is a method (100) of visualizing a sequence of 3D ultrasound images of an object (10) in motion, wherein said motion is a complex motion composed of motion components from a plurality of origins, the method comprising acquiring (120) said sequence of 3D ultrasound images; providing (130) a motion tracking model modelling a contribution to the complex motion, said contribution originating from a subset of said motion components; determining (150) said complex motion from the first and second 3D ultrasound images; and visualizing (160) a contribution of the motion tracking model to the complex motion of said object in order to obtain a motion-decomposed visualization of said complex motion. A computer program product for
(Continued)

implementing such a method on an ultrasound system and an ultrasound system including such a computer program product are also disclosed.

15 Claims, 10 Drawing Sheets

(51) Int. Cl.
    *G06T 7/20*     (2017.01)
    *G01S 15/89*     (2006.01)
    *G01S 7/52*     (2006.01)
    *A61B 8/14*     (2006.01)
    *G06T 7/00*     (2017.01)

(52) U.S. Cl.
CPC ............ *A61B 8/483* (2013.01); *A61B 8/5207* (2013.01); *A61B 8/5223* (2013.01); *G01S 7/52073* (2013.01); *G01S 7/52074* (2013.01); *G01S 15/8993* (2013.01); *G06T 7/0012* (2013.01); *G06T 7/20* (2013.01); *A61B 8/467* (2013.01); *A61B 8/523* (2013.01); *G06T 2207/10016* (2013.01); *G06T 2207/10132* (2013.01); *G06T 2207/30048* (2013.01)

(58) Field of Classification Search
CPC ......... A61B 8/523; A61B 8/467; A61B 8/483; G06T 7/0012; G06T 7/20; G06T 2207/30048; G06T 2207/10016; G06T 2207/10132; G01S 7/52073; G01S 7/52074; G01S 15/8993; G16H 50/30
See application file for complete search history.

(56) References Cited

U.S. PATENT DOCUMENTS

| | | | |
|---|---|---|---|
| 2005/0074154 A1* | 4/2005 | Georgescu | G06T 7/20 382/128 |
| 2006/0058618 A1 | 3/2006 | Nishiura | |
| 2007/0269092 A1 | 11/2007 | Hill et al. | |
| 2008/0009734 A1* | 1/2008 | Houle | A61B 8/08 600/443 |
| 2008/0146942 A1* | 6/2008 | Dala-Krishna | A61B 6/12 600/466 |
| 2008/0267482 A1 | 10/2008 | Abe et al. | |
| 2008/0294048 A1* | 11/2008 | Salgo | A61B 8/08 600/450 |
| 2009/0318803 A1* | 12/2009 | Abe | A61B 8/08 600/438 |
| 2010/0056919 A1 | 3/2010 | Abe | |
| 2010/0195881 A1 | 8/2010 | Orderud et al. | |
| 2010/0198072 A1* | 8/2010 | Abe | A61B 8/0883 600/443 |
| 2010/0208957 A1 | 8/2010 | Chen et al. | |
| 2010/0256495 A1 | 10/2010 | Kruecker et al. | |
| 2011/0313291 A1 | 12/2011 | Chono | |
| 2013/0338501 A1 | 12/2013 | Clingman | |
| 2014/0031688 A1 | 1/2014 | Perrey et al. | |

FOREIGN PATENT DOCUMENTS

| | | |
|---|---|---|
| JP | 2010000199 A | 1/2010 |
| JP | 2010051731 A | 3/2010 |
| JP | 2010179098 A | 8/2010 |
| JP | 2015198672 A | 11/2015 |

OTHER PUBLICATIONS

Cerqueira et al "Standardized Myocardial Segmentation and Nomenclature for Tomographic Imaging of the Heart" Circulation , Jan. 29, 2002 p. 539-542.

\* cited by examiner

400 ure motion components from a plurality of origins. is another subsequently captured image...

METHOD OF VISUALIZING A SEQUENCE OF ULTRASOUND IMAGES, COMPUTER PROGRAM PRODUCT AND ULTRASOUND SYSTEM

This application is the U.S. National Phase application under 35 U.S.C. § 371 of International Application No. PCT/EP2015/074397, filed on Oct. 21, 2015, which claims the benefit of EP Application Serial No. 14306703.1, filed Oct. 27, 2014. These applications are hereby incorporated by reference herein.

FIELD OF THE INVENTION

The present invention relates to a method of visualizing a sequence of ultrasound images of an object in motion, wherein said motion is a complex motion composed of motion components from a plurality of origins.

The present invention further relates to a computer program product for implementing such a method.

The present invention yet further relates to an ultrasound system for executing such a computer program product.

BACKGROUND OF THE INVENTION

The advent of 3D ultrasound imaging techniques has transformed ultrasound imaging into a powerful diagnostic tool as such techniques provide a powerful visualization tool of the anatomy of a subject under investigation at a fraction of the cost of other diagnostic tools such as MRI. A particularly powerful aspect of ultrasound imaging is the ability to capture tissue motion, which can assist a clinician in diagnostic evaluations of the subject under investigation.

The most common visualization mode used in ultrasound imaging is a 2D image, also referred to as the B-mode. The advent of 3D ultrasound imaging techniques has not changed this because 3D visualization is more difficult to achieve and interpret, and most valuable information is retrieved from inside tissues, so that the cut planes or slices in B-mode allow for a more intuitive retrieval of the information of interest than 3D views. Since ultrasound imaging techniques are able to produce images in real-time or to record time sequences of an anatomical object in motion, important information can also be extracted from the tissue motion of such an object. In such a scenario, the visualization may simply consist of tracing the variations of a line representing a portion of interest of the tissue over time; this visualization mode is also referred to as the M-mode. However, due to probe motion, anatomical motion or both, a plane or line that is fixed in the reference frame of the probe usually is not fixed in the reference frame of the anatomical object of interest.

US 2007/0269092 A1 discloses an ultrasound diagnostic imaging system and method, wherein volumetric data in respect of an anatomical region of interest is acquired throughout a physiological cycle in relation thereto, a 3D view of the volumetric data is built, the motion of a structure of interest (in space and/or time) is analyzed within the volume throughout the above-mentioned physiological cycle, and this motion is used to move a 3D view of the structure of interest, as presented to a user, so that it tracks the structure of interest and retains it centred in the 3D view. This for instance is useful to compensate for out of viewing plane movement of the structure of interest, thereby providing a stabilized view of a region of interest of the structure.

However, the motion of the structure of interest often is a complex motion, wherein different motion components from different origins combine to produce the overall motion of the structure of interest. For instance, when imaging a heart, the overall motion in the 3D image sequence may have a number of origins, such as probe motion, breathing motion and blood pumping motion, i.e. cardiac muscle activity, which in itself is a complex combination of twist and compression in both the longitudinal and radial directions of the heart. In such a situation, motion stabilization may not be sufficient to provide a clinician with a clear picture of the relevant motion.

For instance, a clinician such as a cardiologist may be interested in the motion of the myocardium in a short-axis view of the left ventricle of a heart. A heart 10 is schematically depicted in FIG. 1. Heart motion is usually modelled in the medical community by a combination of simple motions, including a rotation around the main (long) axis 20 of the heart 10. In a normal heart, a twisting and untwisting motion appears around the long axis 20 as the result of different rotation speed and amplitude between the basal and apical areas of the heart 10. This is explained in more detail by Gerald Buckberg et al. in Cardiac Mechanics Revisited: The Relationship of Cardiac Architecture to Ventricular Function, Circulation, 2008; 118: 2571 2587; see in particular page 2573. The clinician may select a 2D view plane 30 or a multi-planar reconstruction view, corresponding to the short-axis view at mid-distance between the septum and the mitral annulus at a given time point in the cardiac cycle, and play a full heart cycle sequence. The apparent motion that is displayed in this 2D view is not the motion of the targeted part of the myocardium because out-of-plane motion of the heart 10 drags the targeted part out of the view.

EP 2 397 076 A1 discloses a medical image processing device comprising an image acquisition unit that acquires three-dimensional image data including a moving organ; an image display unit that displays the three-dimensional image data as a three-dimensional image; an object-to-be-measured setting unit that sets a desired object to be measured on the three-dimensional image displayed on the image display unit; a diagnostic index calculating unit that calculates the amount of displacement of the three-dimensional image data in each time phase for the desired object to be measured and calculates a diagnostic index on the basis of the amount of displacement calculated in each time phase; and a control unit that performs control to display the diagnostic index on the image display unit.

Therefore, it is desirable to have the 2D view follow this out-of-plane motion. However, stabilization techniques cannot be applied for this purpose, as such techniques would completely compensate for the motion of the target tissue, i.e. a complex motion including rigid translation, twist and contraction components, such that the clinician would not see any motion at all. On the other hand, some form of motion compensation is desirable; due to the global motion of the heart 10, differentiating between normal and abnormal twisting/untwisting of such areas can be very difficult. This is problematic, given that these motions are critical indicators of the left ventricular function of the heart 10.

The problem of such global motion is schematically depicted in FIG. 2-4. FIG. 2 schematically depicts an object to be visualized in a 3D imaging sequence, such as the heart, which object comprises a plurality of regions 32 of interest, e.g. apical and basal regions of the heart oriented along the long axis 20, wherein within such a region of interest, features 34 of interest may be present, such as different sections of the myocardium within a single region. FIG. 2 schematically depicts the object as captured in the 3D imaging sequence at point in time t1. FIG. 3 schematically depicts the object as captured in the 3D imaging sequence at point in time t2. By comparing FIG. 2 and FIG. 3, it will be apparent that the object of interest has undergone a complex motion in which the object as a whole has been displaced and rotated, wherein regions 32 of interest in addition have rotated relative to each other and wherein features 34 within regions 32 furthermore have moved relative to other parts of the region 32.

Consequently, when the motion of the object under investigation is visualized, it is difficult for the clinician to draw meaningful conclusions from the visualized motion. For example, left ventricle motion may be visualized using the well-known myocardial segmented visualization model of the left ventricle of the American Heart Association as originally published in Circulation, 2002, 105, pages 539-542. Such a short-axis visualization is schematically depicted in FIG. 4, which depicts the basal plane 41 and apical plane 42 of the left ventricle in such a segmented visualization as derived from the 3D ultrasound image sequence including the 3D images captured at t=t1 and t=t2 respectively.

As can be seen from comparing these segmented visualizations, the myocardium in both the basal plane 41 and the apical plane 42 has been subjected to a degree of rotation $\theta_a$ and $\theta_b$ respectively from t1 to t2, but due to the fact that this rotation is a complex rotation composed of a plurality of rotational components, it is impossible for the clinician to determine if there is a difference in rotation between the basal plane 41 and apical plane 42 originating from cardiac twisting. In other words, these visualizations do not allow the clinician to easily differentiate between normal and abnormal twisting/untwisting of such areas.

SUMMARY OF THE INVENTION

The present invention seeks to provide a method of visualizing a sequence of ultrasound images in which such complex motions can be decomposed.

The present invention further seeks to provide a computer program product comprising a computer-readable medium containing computer program code for implementing such a method when executed on a processor of an ultrasound system.

The present invention yet further seeks to provide an ultrasound system comprising such a computer program product.

According to a first aspect, there is provided a method of visualizing a sequence of 3D ultrasound images of an object in motion, wherein said motion is a complex motion composed of motion components from a plurality of origins, the method comprising acquiring said sequence of 3D ultrasound images, said sequence including a first 3D ultrasound image acquired at a first point in time and a second 3D ultrasound image acquired at a second point in time; providing a motion tracking model modelling a contribution to the complex motion, said contribution originating from a subset of said motion components; determining said complex motion from the first and second 3D ultrasound images; and visualizing a contribution of the motion tracking model to the complex motion of said object in order to obtain a motion-decomposed visualization of said complex motion. The complex motion is e.g. formed of translational and rotational motion components.

By providing a motion tracking model that tracks or models part of the complex motion to which an object in motion such as a heart is subjected during the sequence, the complex motion may be decomposed such that in a visualization the contribution of the motion tracking model becomes apparent to the user evaluating the visualized motion. Such decomposition may facilitate the user, e.g. a clinician such as a cardiologist, to more easily reach diagnostically relevant conclusions. The complex motion may be decomposed such that the translational and rotational motion components become apparent to the user.

In an embodiment, the 3D ultrasound images are decomposable in a plurality of slices each depicting a different segment of the object, wherein the motion tracking model comprises a reference rotation and wherein said visualizing comprises visualizing a rotation of the segments of said object relative to said reference rotation. The complex rotation depicted in such slices, e.g. short axis views of the heart, may be decomposed in this manner, e.g. by providing a motion tracking model that tracks or simulates global rotation, such that it becomes more apparent how these segments rotate relative to each other, which will aid the user to determine if the relative rotation, e.g. twisting/untwisting of the myocardium, is abnormal.

The reference rotation may be associated with one of said segments. For instance, the reference rotation may represent a global rotation component as well as a normal local rotation component of the segment such that the motion-decomposed visualization of the segment visualizes a deviation from the expected local rotation of the segment, with the motion-decomposed visualization of the rotation of the remainder of the segments depicting rotation relative to the expected normal rotation of the segment with which the reference rotation is associated.

In an embodiment, the motion tracking model may be defined by the user, for instance using a graphical user interface. In this embodiment, providing the motion tracking model may comprise selecting a first point and a second point in the first 3D ultrasound image acquired at the first point in time to define a reference axis in said first 3D ultrasound image, and selecting a third point in said first 3D ultrasound image for tracking a rotation around said reference axis; tracking the motion of the first point, second point and third point by comparing the second 3D ultrasound image acquired at the second point in time with the first 3D ultrasound image; and defining the motion tracking model from said tracked motion of the first point, second point and third point. This for instance facilitates the definition of a reference rotation for a segment of the object in motion in which the third point is located, such that the rotation relative to this reference rotation may be visualized for the other segments. Moreover, where such a reference rotation depicts a global rotation, motions that are internal to the segment containing the third point, e.g. local contractions and so on may be visualized more clearly.

Alternatively, providing the motion tracking model may comprise providing a predefined motion tracking model, for instance a tracking model that approximates global motion of the object in motion.

In an embodiment, the predefined motion tracking model comprises a translational component and a plurality of rotational components along a central axis, said rotational components modelling rotation of different regions of the object along said central axis. This for instance may be used when decomposing the complex motion of a heart, wherein the different rotational components simulate normal twisting/untwisting of the heart during the cardiac cycle. The use of such a model in the motion-decomposed visualization of the cardiac motion immediately highlights if such motion deviates from normal behaviour.

The visualizing may comprise subtracting the motion tracking model from the complex motion; and displaying the subtraction result to obtain said motion-decomposed visualization of said complex motion. This has the advantage that the user is presented with a visualization of the decomposition result, which may allow the user to reach clinically relevant conclusions in a more straightforward manner.

Alternatively, the visualizing may comprise displaying said complex motion; and displaying a representation of the motion tracking model as an overlay on said displayed complex motion. This for instance allows the user to readily distinguish between the motion component modelled by the motion tracking model and the overall motion for a particular segment of the object under investigation.

In an embodiment, the visualization is a B-mode visualization of a left ventricle of a heart in short axis view, said visualization being based on a segmented graphical representation of the myocardium. Such a representation has the advantage that the user can easily determine the amount of twisting/untwisting by the graphical representation of the myocardium in the visualization.

The step of providing the motion tracking model may comprise selecting a motion tracking model on a graphical user interface, for instance by selecting a predefined motion tracking model from a library of such motion tracking models or by defining points to be tracked in the sequence of 3D ultrasound images as previously explained.

In an embodiment, the method further comprises adjusting the motion tracking model on said graphical user interface following said visualization; and visualizing a contribution of the adjusted motion tracking model to the complex motion of said object in order to obtain an adjusted motion-decomposed visualization of said complex motion. This allows the user to interactively apply a motion decomposition to the sequence of 3D ultrasound images by scaling the contribution of the motion tracking model to the overall complex motion, thereby fine tuning the motion tracking model and motion decomposition, which may assist a user in a better understanding of the decomposition of the various contributions to the overall complex motion of the object under investigation.

According to another aspect, there is provided a computer program product including a computer-readable medium comprising computer program code for, when executed on a processor of an ultrasound system, implementing the method according to one or more of the above embodiments. Such a computer program product facilitates the user of such an ultrasound system to evaluate a sequence of 3D ultrasound images in a more straightforward manner.

According to yet another aspect, there is provided an ultrasound system comprising the aforementioned computer program product, a probe for transmitting ultrasound waves and collecting a sequence of ultrasound echoes in response to the transmitted ultrasound waves; and a processor for generating ultrasound images from the collected ultrasound echoes, wherein the processor is adapted to execute said computer program code. Such an ultrasound system allows its user to evaluate a sequence of 3D ultrasound images in a more straightforward manner.

The ultrasound system may further comprise a workstation for displaying the motion-decomposed visualization of said complex motion, said processor being adapted to control said workstation.

The ultrasound system may further comprising a graphical user interface for defining and/or adjusting the motion tracking model on said workstation.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
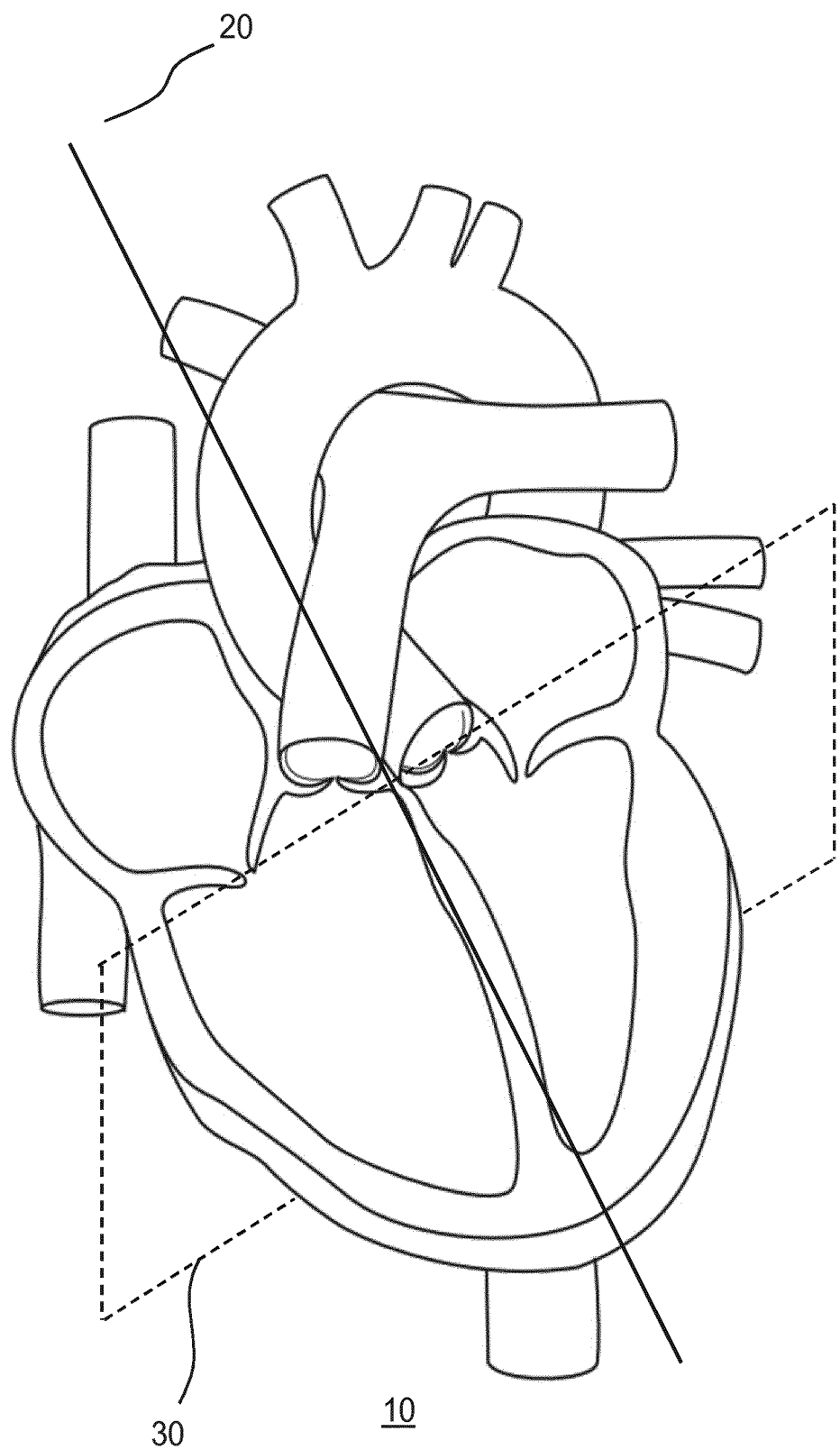
FIG. 1 schematically depicts a cross-section of a human heart.
Figure 2:
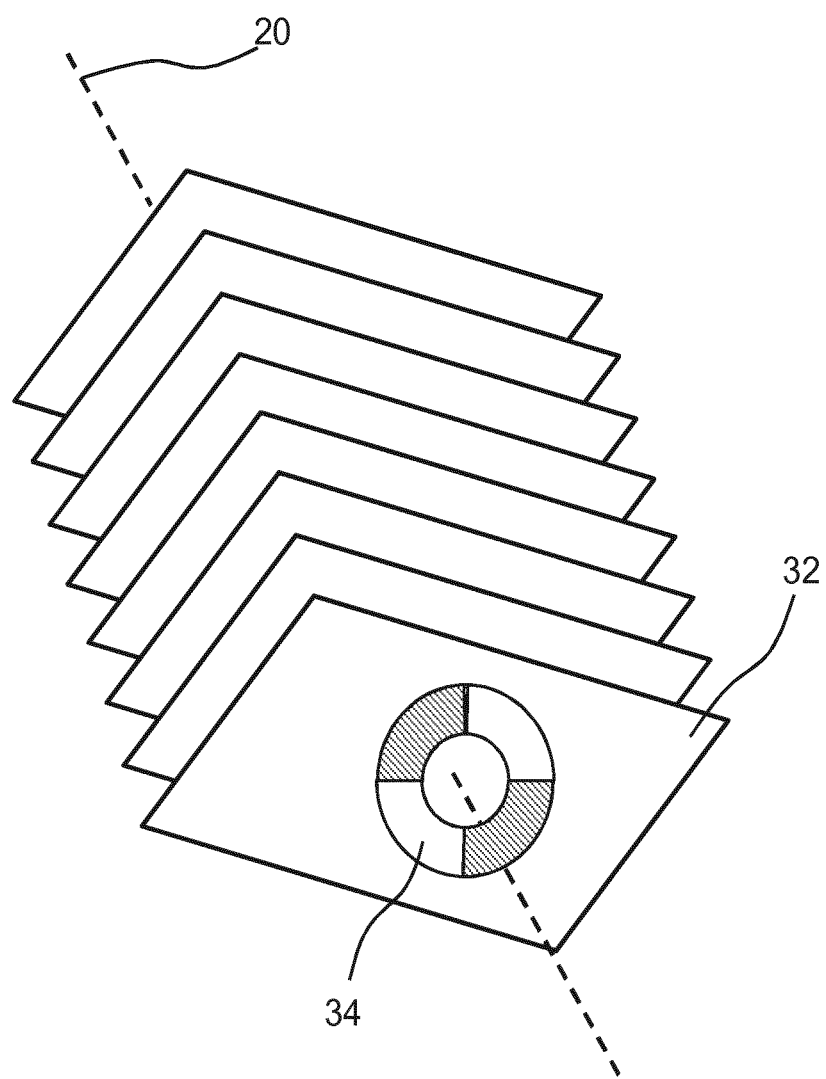
FIGS. 2 and 3 schematically depict complex motion of an object in motion such as a human heart as captured by a sequence of 3D ultrasound images.
Figure 3:
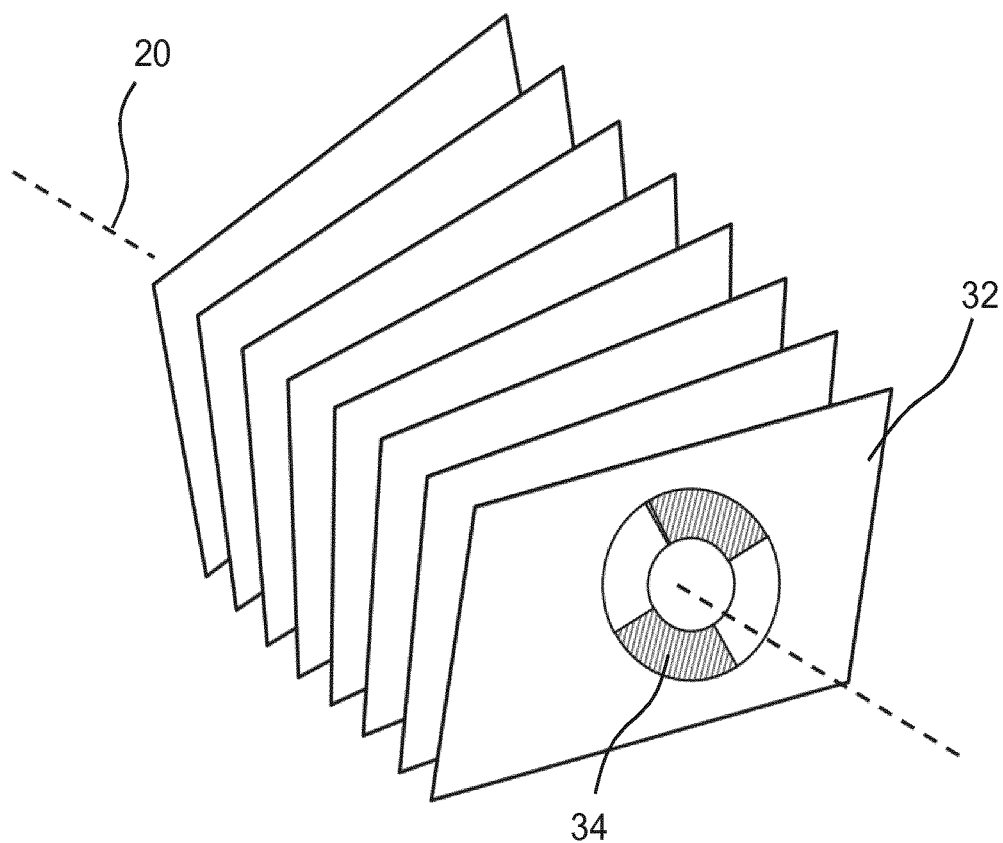

It should be understood that the Figures are merely schematic and are not drawn to scale. It should also be understood that the same reference numerals are used throughout the Figures to indicate the same or similar parts unless indicated otherwise.

Figure 5:
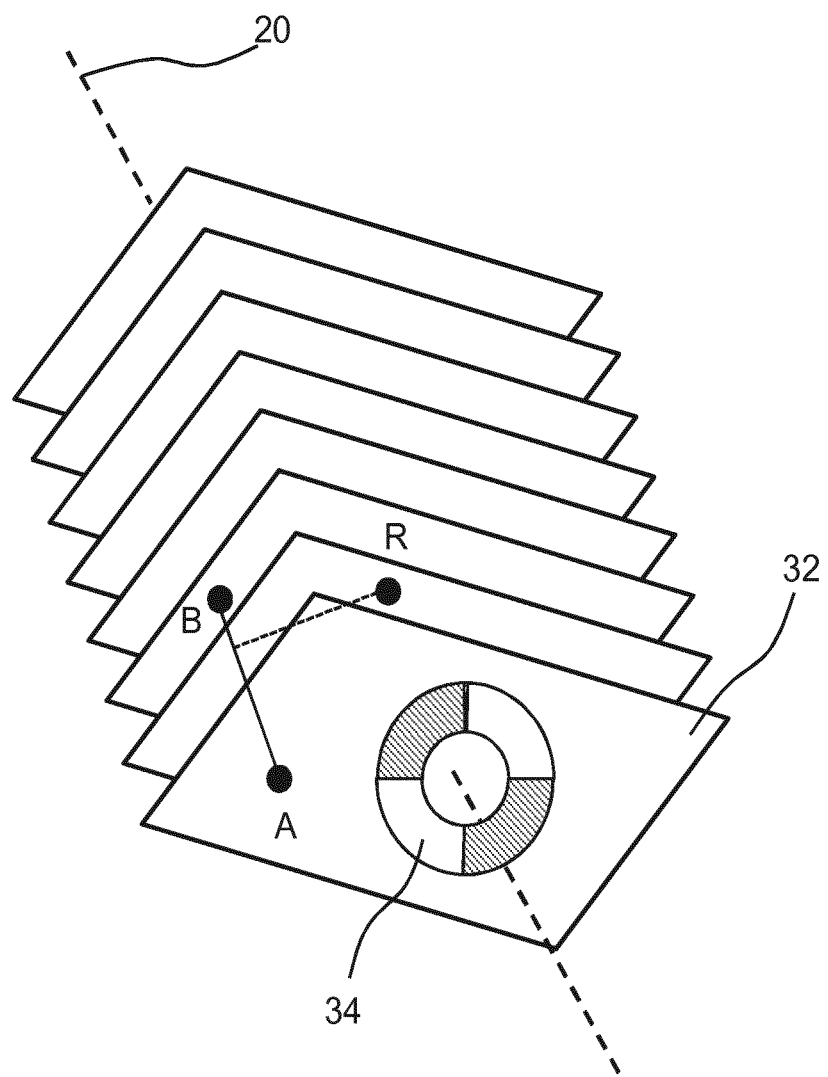
FIGS. 5 and 6 schematically depict the tracking of a motion component of an object in motion according to an embodiment.

FIG. 5 schematically depicts a 3D ultrasound image of a heart in motion at a first point in time t=t1, wherein the heart is schematically represented by a plurality of short axis slices 32 along the long axis 20 wherein each slice 32 depicts a different slice of the heart along the long axis 20. Each slice 32 may comprise a region 34 of interest, e.g. a left ventricle view including the myocardium for evaluation of myocardial behaviour during the 3D ultrasound image sequence of the heart.

In accordance with an embodiment, the user may create a user-defined motion tracking model by selecting a first point A and a second point B in the 3D ultrasound image at t=t1, wherein points A and B define a reference axis in the ultrasound image, which may be used to track rotation around this reference axis. To this end, the user may further define a third point C located in one of the slices 32, wherein the thus defined reference frame may be used to track the motion of this reference frame throughout the sequence of 3D ultrasound images. By an informed selection of points A, B and C, e.g. by a clinician such as a cardiologist, the motion to which these points have been subjected from t1 to t2 may be used as a reference motion, i.e. a motion tracking model, wherein motions within the object under investigation may be decomposed as motions relative to this reference motion.

Figure 6:
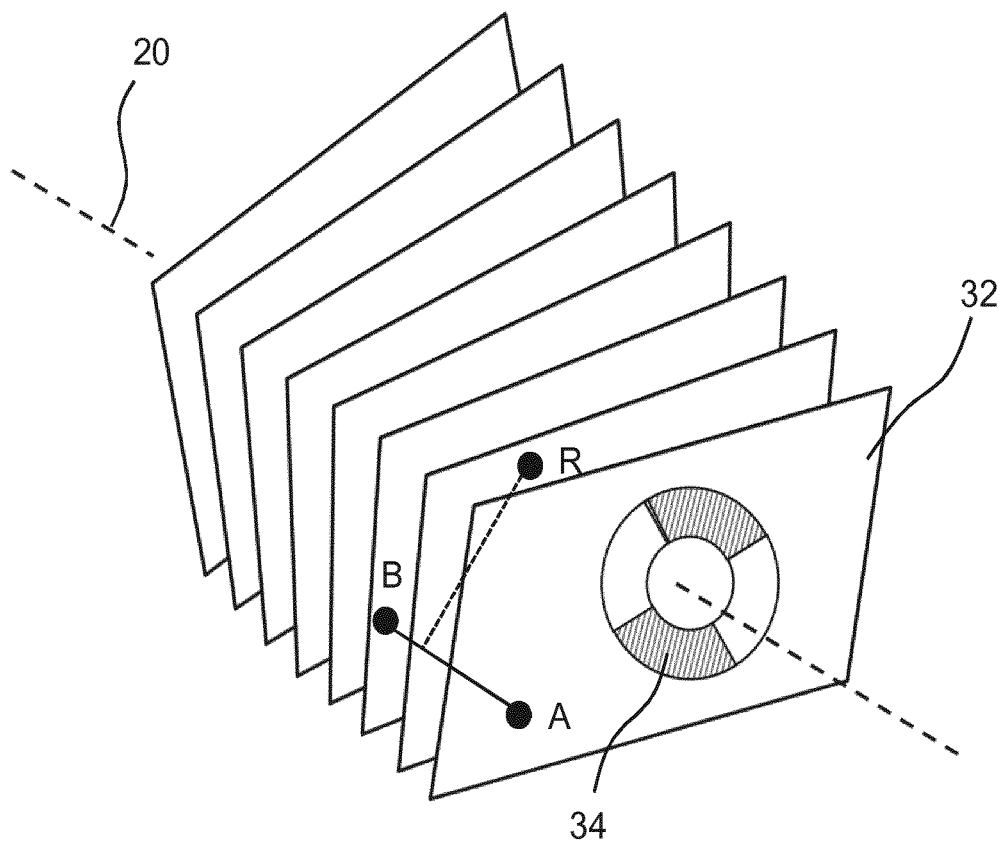

The motion to be tracked is schematically depicted in FIG. 6, which schematically depicts a second 3D ultrasound image of the sequence at point in time t=t2, in which the heart has undergone a complex motion compared to the point in time t=t1. The motion to which the reference frame defined by points A, B and C have been subjected may be tracked in the sequence of 3D ultrasound images.

Figure 7:
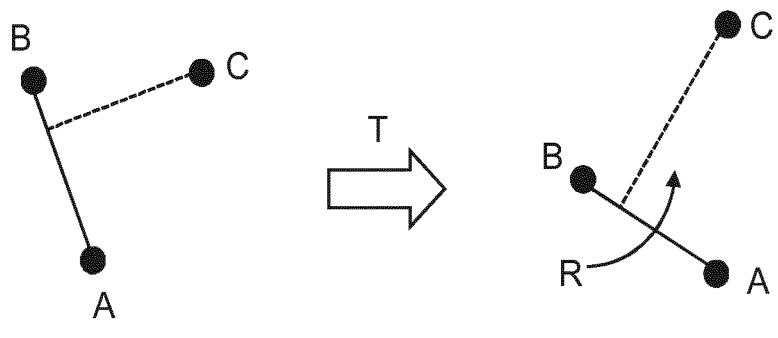
FIG. 7 schematically depicts an aspect of defining a motion tracking model based on the tracking of the motion component as depicted in FIGS. 5 and 6.

FIG. 7 schematically depicts the tracked motion of the reference frame defined by points A, B and C. The tracked motion can be seen as a composition of the affine transform T that follows the axis A-B from time t1 to t2 and a model of rotation R around this axis, wherein T and R have been measured from the 3D ultrasound image sequence, with T being measured from the translation of the axis A-B and R being measured from the rotation of point C around the axis A-B to compose the motion tracking model to be used in the motion decomposition of the complex motion of the object under investigation.

Figure 4:
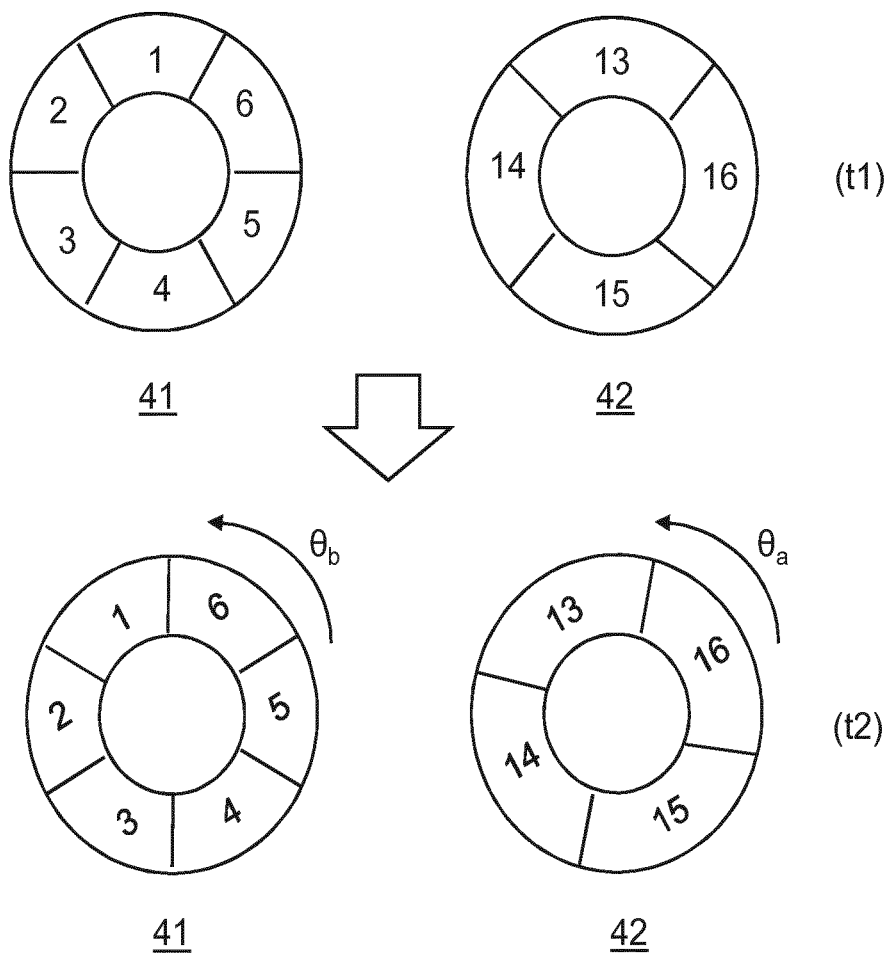
FIG. 4 is a visualization of such complex motion using a segmented graphical representation.

In an embodiment in which the 3D ultrasound image sequence captures a heart in motion, a particularly advantageous visualization of the cardiac motion, e.g. to visualize twisting/untwisting, is the 2D short-axis view (SA), i.e. the plane 30 orthogonal to the main axis 20 of the heart 10 as shown in FIG. 1. For instance, a particularly intuitive visualization is obtained when using the aforementioned 17 segment-based myocardium visualization model of the AHA, as this facilitates accurate location of the SA planes, e.g. the basal plane 41 and the apical plane 42. Such a 2D short axis view may be transferred into such a segmented visualization model in any suitable manner, as is well-known per se. For instance, the various AHA segments may be identified in various short axis views of a first 3D image, and associated with objects, e.g. tissue parts, that can be tracked using available tracking techniques, after which the thus associated segments may be tracked in the 3D image sequence by tracking the associated objects. As previously explained with the aid of FIG. 4, it is clear when evaluating the complex motion visualized in this segmented model that both the basal plane 41 and the apical plane 42 undergo a rotation, but it is virtually impossible to determine if this rotation is more or less than a normal rotation of these planes over the time interval t1-t2.

Figure 8:
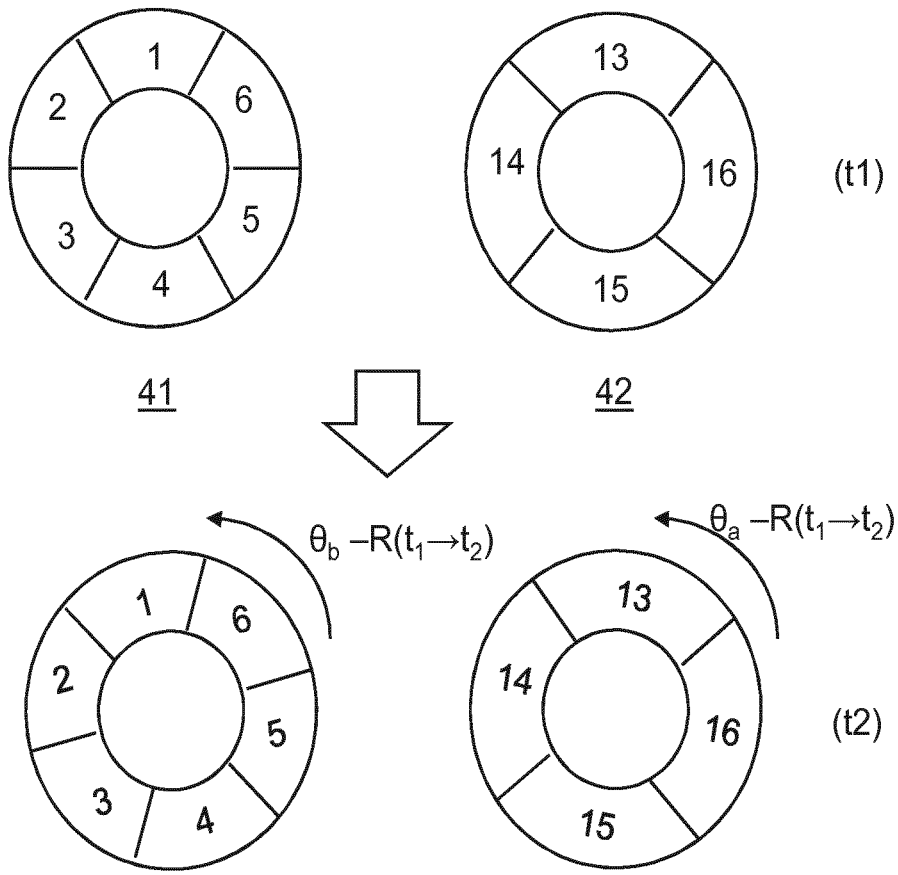
FIG. 8 schematically depicts a visualization of a motion-decomposed motion of a heart motion captured in a 3D ultrasound image sequence according to an embodiment.

In an embodiment, the chosen visualization (here a segmented visualization by way of non-limiting example) may be adapted by subtracting the motion tracking model from the overall motion captured in the 3D ultrasound image sequence in order to obtain a motion-decomposed visualization in which only a part of the overall (complex) motion is visualized. Using the example previously depicted in FIG. 4, a motion-decomposed visualization as schematically depicted in FIG. 8 may be obtained. By subtracting the contribution of the motion tracking model from the overall motion, in particular the rotational component $R(t_1 \rightarrow t_2)$ modelling the rotational component of the motion tracking model from the overall rotations $\theta_b$ and $\theta_a$ respectively, it becomes immediately apparent that the remaining rotation component is larger for the basal plane 41 compared to the apical plane 42. This demonstrates that the use of such a motion tracking model can assist the user in obtaining a more straightforward visualization of decomposed motion components, e.g. motion components of interest such as diagnostically relevant motion components.

Figure 9:
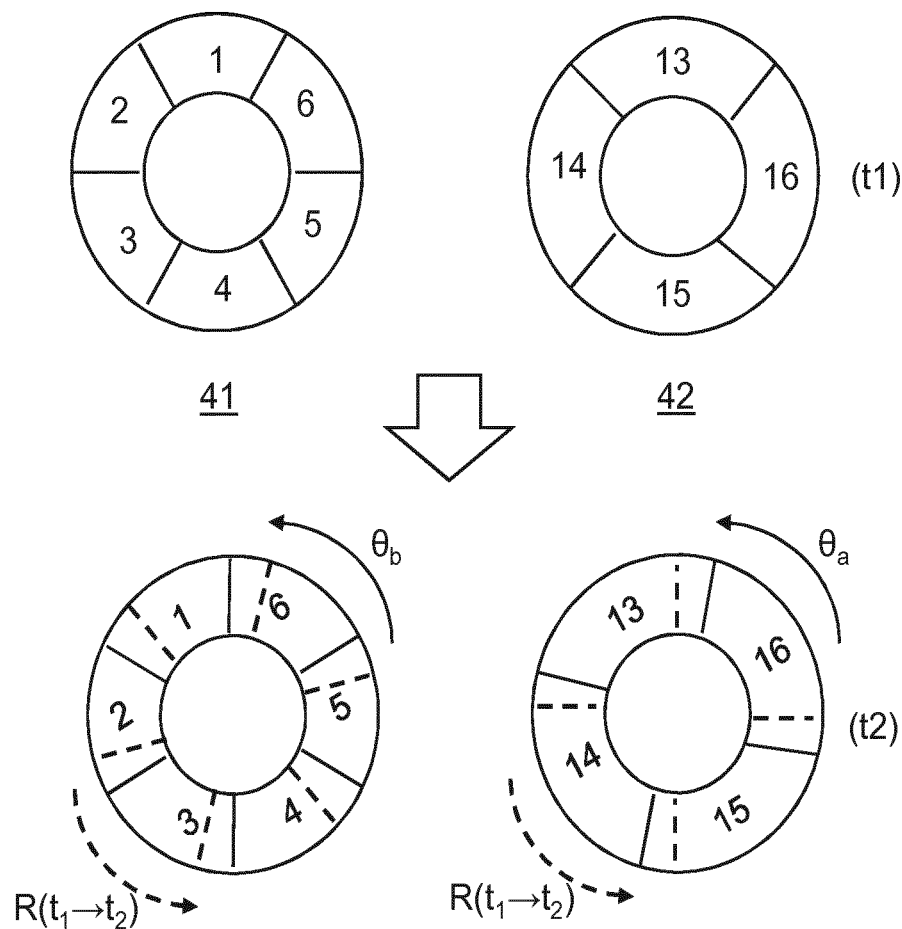
FIG. 9 schematically depicts a visualization of a motion-decomposed motion of a heart motion captured in a 3D ultrasound image sequence according to another embodiment.

In an alternative embodiment, the chosen visualization (here a segmented visualization by way of non-limiting example) may be adapted by overlaying the motion tracking model onto the overall motion captured in the 3D ultrasound image sequence in order to obtain a motion-decomposed visualization in which the contribution of the motion tracking model to the overall (complex) motion is visualized. This is schematically depicted in FIG. 9, in which the dashed lines in the anatomical model representation at t=t2 depict the contribution of the rotational component $R(t_1 \rightarrow t_2)$ of the motion tracking model to the overall visualized rotation. In addition to clearly demonstrating that the remaining rotation component is larger for the basal plane 41 compared to the apical plane 42, this furthermore visualizes the contribution of the tracked motion to the overall motion captured in the 3D ultrasound image sequence.

At this point, it is noted that the user-defined motion tracking model is particularly suitable to visualize rotation of further parts of the object under investigation such as the heart relative to a tracked rotation of a particular part of the object, particularly the segment of the object containing the user-selected point C, which may be considered a reference segment. As will be understood by the skilled person, when applying the motion tracking model to the complex motion of the reference segment, this reference segment will appear as a stationary segment in which only motions relative to the tracked rotation, e.g. localized tissue rotations or contractions, may be visualized in the motion-decomposed view.

However, because segments of the object under investigation other than a reference segment may rotate at different speeds than the reference segment, such differences in speed, i.e. relative rotations, will become apparent when applying the motion tracking model to the tracked overall motion in order to obtain the motion-decomposed visualization of the object of interest. In other words, the motion tracking model may be considered to comprise a reference rotation, i.e. the tracked rotation $R(t_1 \rightarrow t_2)$, wherein the motion-decomposed visualization comprises the visualization a rotation of the segments of said object relative to this reference rotation.

At this point, it is noted that the motion tracking model does not have to be user-defined. Alternatively, the motion tracking model may be automatically generated from the sequence of 3D ultrasound images using well-known motion estimation techniques such as tissue tracking, speckle tracking and so on. As such motion estimation techniques are well-known per se, they will not be explained in further detail for the sake of brevity only. In yet another embodiment, an a priori motion tracking model may be provided, which for instance may be a model representative of a normal motion of the object under investigation, e.g. the normal or expected motion of a healthy heart in such a sequence. In order to make such an a priori model more realistic, the model may comprise different rotational components around a central axis, e.g. at different locations along the long axis 20 in case the model represents normal heart motion in order to reflect the different degrees of twisting/untwisting of the different short axis segments of the heart along the long axis 20. Such an a priori model can be seen to provide a set of reference rotation speeds for the heart, wherein application of the model to an actual sequence of 3D ultrasound images capturing the complex motion of the heart throughout the sequence may highlight deviations in the expected degree of rotation for particular segments of the heart.

In an embodiment, such an a priori or predefined motion tracking model may be used in combination with a further tracking model in which for instance translational motion, e.g. the displacement of the axis A-B, is separately compensated for, such that the a priori motion tracking model may be based on one or more rotational components only and may be applied once the translational motion of the object of interest in the sequence of 3D ultrasound images has been compensated for.

In an embodiment, the motion tracking model may be scalable. In other words, a user may adjust the contribution of the various components, e.g. translational and rotational components, such as the displacement of axis A-B and the rotation R around this axis as depicted in FIG. 7 such that the user can interactively adjust the motion tracking model and update the visualization of the 3D ultrasound image sequence in accordance with the updated motion tracking model. This for instance allows the user to interactively select a particular segment of an object of interest as a reference segment by adjusting the motion tracking model such that the selected segment becomes stationary in the visualization, such that the user can evaluate motions in other parts of the object of interest, e.g. a heart, relative to the interactively selected reference segment.

The user may make such adjustments to the motion tracking model in any suitable manner. By way of non-limiting example, a graphical user interface may be provided that allows the user to make the desired adjustments, for instance by representing the various components of the motion tracking model as dials, sliders or the like in the graphical user interface, wherein the user may adjust these components by adjusting the dials, sliders or the like, which adjustments trigger the generation of an updated visualization of the object under investigation based on the adjustments made to the motion tracking model.

In the above description, aspects of the present invention have been explained by way of a visualization mode in 2D short axis view by way of non-limiting example only. It should be understood that the teachings of the present invention may be applied to any suitable visualization mode, including but not exclusively limited to a 1-D visualization mode (M-mode), 2D visualization mode (B-mode) or 3D visualization mode (volume rendering). As previously explained, the visualization mode may be defined either manually from a point in time in the 3D ultrasound image sequence or from an anatomical model or a reference that is automatically adapted to the actual sequence, e.g. the aforementioned segmented visualization of a left ventricle of a heart in 2D short axis view.

Figure 10:
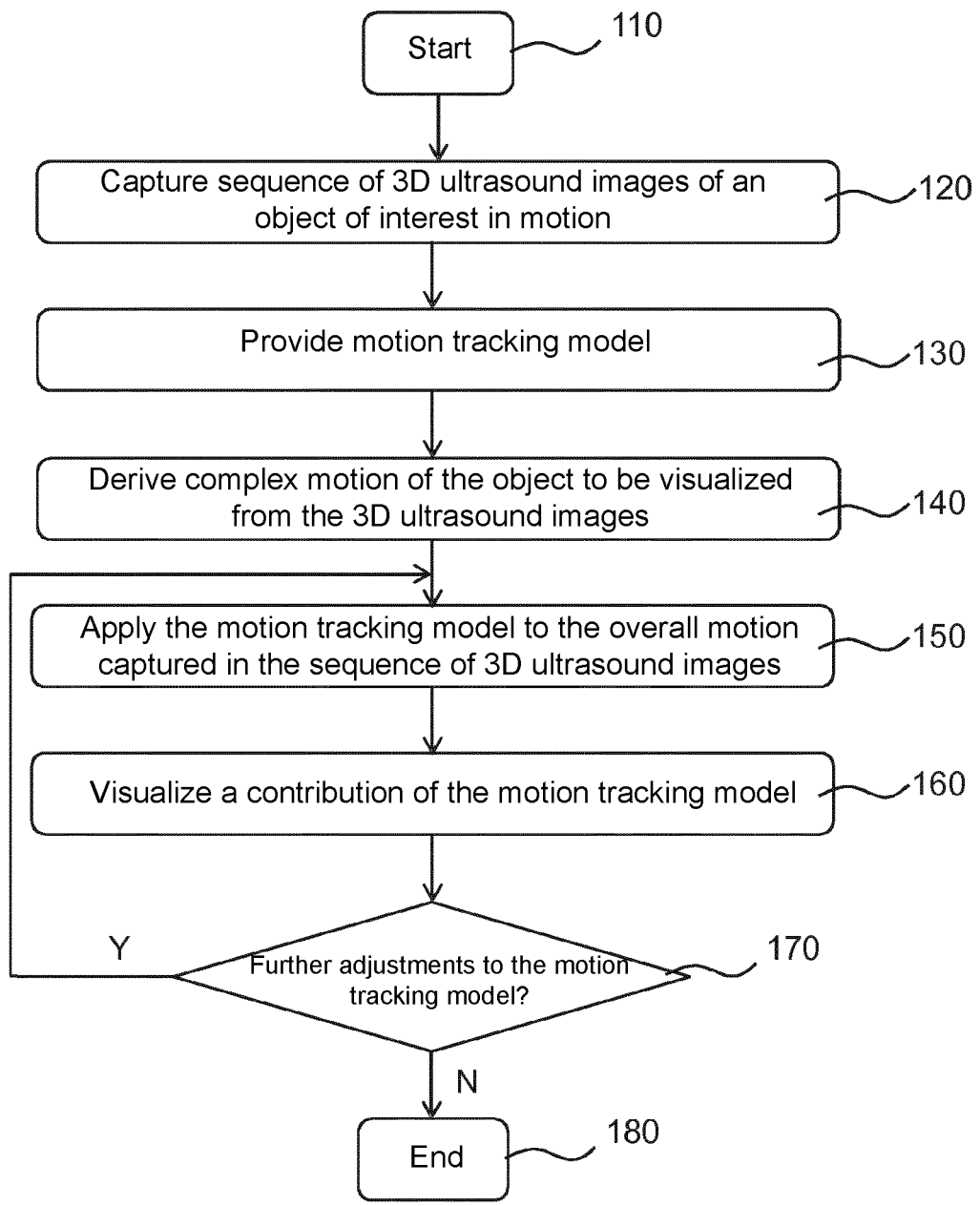
FIG. 10 is a flowchart of a method according to an embodiment.

In summary, the various embodiments of the visualization method 100 described in detail above may be summarized by the flow chart depicted in FIG. 10. The method 100 starts in step 110, e.g. by initializing an ultrasound system for capturing a sequence of 3D ultrasound images of an object of interest in motion, such as a heart. The method then proceeds to step 120 in which the sequence of 3D ultrasound images of the object of interest in motion is captured. Such a sequence may be captured in any suitable manner as is well-known per se to the skilled person.

In step 130, the motion tracking model is provided. As previously explained in more detail, this for instance may be a user-defined motion tracking model, an automatically generated motion tracking model or an a priori (predefined) motion tracking model, such as a motion tracking model including a reference rotation such that subsequent motion-decomposed visualization of the complex motion of the object under investigation may comprise visualizing a rotation of various segments of said object relative to said reference rotation.

Next, the complex motion of the object to be visualized is derived from the 3D sequence of ultrasound images in step 140; this is known per se and will not be explained in further detail for the sake of brevity only. It is noted that although in method 100 the provision of the motion tracking model is performed after capturing the sequence of 3D ultrasound images and before the determination of the complex motion, it is equally feasible that the motion tracking model for instance is provided after the determination of the complex motion in step 140 or before step 120, for instance when using an a priori motion tracking model. In step 150, the motion tracking model is applied to the overall motion captured in the sequence of 3D ultrasound images, for instance by subtracting the motion tracking model from the overall motion or by overlaying a visualization of the motion tracking model or a visualization of the overall motion as previously explained after which the result of step 150 is visualized in step 160, for instance on a display of an on cart or off-cart workstation of ultrasound system, or on any other display for displaying such a visualization result. As previously explained, any suitable visualization form may be chosen for this purpose.

In an optional embodiment, the method 100 further comprises a step 170 in which a user may decide to adjust the motion tracking model as previously explained, in which case the method may return to step 150 and apply the adjusted motion tracking model to the overall motion and visualize the result in step 160. If step 170 is not available or if the user decides that no further adjustments to the motion tracking model are of interest are required, the method may terminate in step 180.

Figure 11:
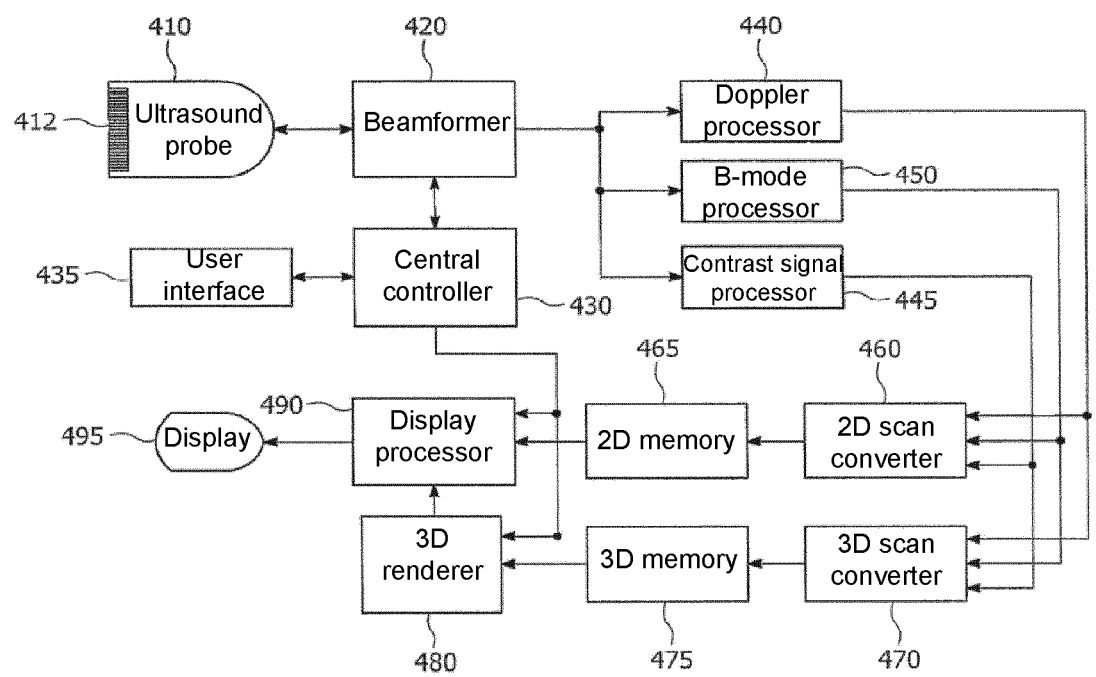
FIG. 11 schematically depicts an ultrasound system according to an example embodiment.

FIG. 11 schematically depicts an example embodiment of an ultrasound system 400 that may be used in accordance with the visualization methods of the present invention. The ultrasound system 400 may be a system for acquiring real-time 3D cardiac images, either as 2D tomographic slices or as volumetric image data. In operation, a probe or scanhead 410 which includes a 1D or 2D array transducer 412 transmits ultrasonic waves and receives ultrasonic echo signals. This transmission and reception is performed under control of a beamformer 420 which possesses received echo signals to form coherent beams or raw echo signals from the anatomy being scanned. The echo information from the beamformer is then processed by the B-mode processor, 450, the Doppler processor, 440, and, if contrast agents are used during imaging, the contrast signal processor, 445. The B-Mode processor performs functions that include, but are not limited to, filtering, frequency and spatial compounding, harmonic data processing and other B-Mode functions well known in the art. The Doppler processor applies conventional Doppler processing to the echoes to produce velocity and Doppler power signals. The contrast processor applies specific processing to echo signals that are obtained when contrast agents are present in the tissue being scanned. The processed data is then passed through either a 2D scan converter 460 or a 3D scan converter 470, depending on whether a 2D tomographic or 3D volumetric region of tissue is being imaged. The scan converter geometrically corrects the data from the linear or polar geometry that the scanhead acquired the beams in, to a Cartesian format (x,y or x,y,z) with appropriate scaling in each dimension. Each scan converted image or 3D volume is then placed in a 2D memory, 465, or 3D volume memory, 475. The memory 465 blocks store a few seconds up to several minutes worth of recent 2D or 3D data, depending on the type of data being acquired.

The Volume MPR slice display processor and 3D renderer, 480, processes volume data from the 3D volume memory based on the central controller, 430, and user input from the user interface, 435, to provide one or several 2D MPR slice images and/or a volume rendered image of the 3D volume from a given viewpoint using methods well known in the art. The display processor, 490, based on input from the central controller, 430, takes 2D images either from the 2D memory 465 or the volume MPR slice view processor and 3D rendered, adds graphics overlays and text annotation (e.g. patient information) and passes the composted images on to the display, 495, for presentation to the operator. The central controller can direct the display processor to display the most recently acquired data in memory as a real-time display, or it can replay sequences of older 2D or 3D volume data. At least one of the Volume MPR slice display processor and 3D renderer 480 and the display processor 490 may be adapted to execute the computer program code embodying the method according to embodiments of the present invention. In an embodiment, the Volume MPR slice display processor and 3D renderer 480 and the display processor 490 cooperate to generate the motion-decomposed visualization of the image(s) of interest.

It should be understood that the ultrasound system 400 is merely an example of an ultrasound systems that may be used to acquire a sequence of 3D ultrasound images in accordance with embodiments of the method of the present invention. The exact implementation of the ultrasound system 400 is largely irrelevant to the present invention, as long as the ultrasound system is capable of implementing the method 100. It will therefore be understood by the skilled person that any suitable ultrasound system may be used.

Aspects of the present invention may be embodied as a system, method or computer program product. Aspects of the present invention may take the form of a computer program product embodied in one or more computer-readable medium(s) having computer readable program code embodied thereon for implementing the visualization method according to various aspects of the present invention when executed on a suitable processor, such as the processor of an ultrasound system.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection; for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out the method of the present invention by execution on a suitable processor may be written in any combination of one or more programming languages, including an object oriented programming language such as Java, Smalltalk, C++ or the like and conventional procedural programming languages, such as the "C" programming language or similar programming languages. The program code may execute entirely on the processor as a stand-alone software package, or may be executed partly on the processor and partly on a remote server. In the latter scenario, the remote server may be connected to the processor through any type of network, including a local area network (LAN) or a wide area network (WAN), or the connection may be made to an external computer, e.g. through the Internet using an Internet Service Provider.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on one or more processors of the ultrasound system 400, such that the instructions create means for implementing the functions/acts specified in the flowchart and/or block diagram block or blocks. These computer program instructions may also be stored in a computer-readable medium that can direct the system 400 to function in a particular manner.

The computer program instructions may be loaded onto the one or more processors to cause a series of operational steps to be performed on the one or more processors, to produce a computer-implemented process such that the instructions which execute on the one of more processors provide processes for implementing the functions/acts specified in the flowchart and/or figures depicting the motion tracking and visualization results. The computer program product may form part of the ultrasound system 400, e.g. may be installed on the ultrasound system 400.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A method of visualizing a sequence of 3D ultrasound images, the method comprising:
   acquiring a sequence of 3D ultrasound images of an object in complex motion, the complex motion comprising motion components from a plurality of origins, wherein the sequence includes a first 3D ultrasound image acquired at a first point in time and a second 3D ultrasound image acquired at a second point in time, wherein each of the first and second 3D ultrasound images includes a plurality of regions of interest (ROIs) that divide the object into multiple segments;
   determining, from the first and second 3D ultrasound images, the complex motion of the object by determining relative motion of the respective segments in each of the plurality of ROIs in the first and second 3D ultrasound images;
   modelling a first subset of the motion components of the complex motion corresponding to a reference motion of the object between the first and second 3D ultrasound images; and
   comparing the complex motion of the object to the reference motion to provide a motion-decomposed visualization of the complex motion of the object by subtracting the reference motion from the complex motion and displaying the subtraction result to provide the motion-decomposed visualization of the complex motion.

2. The method of claim 1, wherein the plurality of ROIs comprise a plurality of slices, each depicting a different segment of the object, wherein the reference motion comprises a reference rotation (R), and wherein said motion-decomposed visualization comprises visualizing a rotation of the segments of the object relative to the reference rotation.

3. The method of claim 2, wherein the reference rotation (R) is associated with one of said segments.

4. The method of claim 1, wherein the modelling the first subset of the motion components comprises:
   selecting a first point (A) and a second point (B) in the first 3D ultrasound image acquired at the first point in time to define a reference axis (A-B) in the first 3D ultrasound image, and selecting a third point (C) in the first 3D ultrasound image for tracking a rotation (R) around said reference axis; and
   tracking the motion of the first point, the second point and the third point by comparing the second 3D ultrasound image acquired at the second point in time with the first 3D ultrasound image.

5. The method of claim 1, wherein modelling of the first subset of the motion components comprises providing a predefined motion tracking model.

6. The method of claim 5, wherein the predefined motion tracking model comprises a translational component and a plurality of rotational components along a central axis, said rotational components modelling rotation of different regions of the object along said central axis.

7. The method of claim 1, wherein said comparing the complex motion of the object to the reference motion to provide the motion-decomposed visualization comprises:
   displaying the complex motion; and
   displaying a representation of the reference motion as an overlay on the displayed complex motion.

8. The method of claim 1, wherein the motion-decomposed visualization is a B-mode visualization of a left ventricle of a heart in short axis view, said motion-decomposed visualization being based on a segmented graphical representation of the myocardium.

9. The method of claim 8, wherein the step of modelling the first subset of motion components of the complex motion comprises selecting a motion tracking model on a graphical user interface.

10. The method of claim 9, further comprising:
    adjusting the motion tracking model on said graphical user interface following said motion-decomposed visualization; and
    visualizing a contribution of the adjusted motion tracking model to the complex motion of said object in order to obtain an adjusted motion-decomposed visualization of said complex motion.

11. A computer program product including a non-transitory computer-readable medium comprising computer program code for, when executed on a processor of an ultrasound system, implementing the method of claim 1.

12. An ultrasound system comprising:
    the computer program product of claim 11;
    a probe for transmitting ultrasound waves and collecting a sequence of ultrasound echoes in response to the transmitted ultrasound waves; and
    a processor for generating the sequence of 3D ultrasound images from the collected ultrasound echoes, wherein the processor is adapted to execute said computer program code.

13. The ultrasound system of claim 12, further comprising a workstation for displaying the motion-decomposed visualization of said complex motion, said processor being adapted to control said workstation.

14. The ultrasound system of claim 13, further comprising a graphical user interface for defining and/or adjusting the modelling of the first subset of motion components on said workstation.

15. The method of claim 1, wherein the modeling of the first subset of motion components comprises defining a reference frame comprising at least two points within a given ROI and at least one point outside of the given ROI, and wherein the reference motion comprising a motion of the reference frame from the first 3D ultrasound image to the second 3D ultrasound image.

* * * * *